United States Patent
Nanjyo

(10) Patent No.: US 6,574,432 B2
(45) Date of Patent: Jun. 3, 2003

(54) FUNDUS CAMERA

(75) Inventor: Tsuguo Nanjyo, Toyohashi (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 09/813,159

(22) Filed: Mar. 21, 2001

(65) Prior Publication Data

US 2003/0068164 A1 Apr. 10, 2003

(30) Foreign Application Priority Data

Mar. 22, 2000 (JP) ........................................ 2000-081047

(51) Int. Cl.⁷ .............................................. G03B 29/00
(52) U.S. Cl. .......................... 396/18; 351/206; 351/213
(58) Field of Search ........................... 396/18; 351/213, 351/206

(56) References Cited

U.S. PATENT DOCUMENTS

| | | | |
|---|---|---|---|
| 4,436,388 A | * 3/1984 | Takahashi et al. | 351/206 |
| 4,439,024 A | * 3/1984 | Ito | 351/207 |
| 4,572,627 A | 2/1986 | Madate et al. | |
| 5,118,179 A | * 6/1992 | Sano et al. | 351/206 |
| 5,163,437 A | 11/1992 | Fuji et al. | |
| 5,302,988 A | 4/1994 | Nanjo | |
| 5,594,512 A | * 1/1997 | Yoneda et al. | 351/206 |
| 5,630,179 A | * 5/1997 | Kishida | 351/206 |
| 5,668,621 A | * 9/1997 | Nanjo | 351/206 |
| 5,841,509 A | * 11/1998 | Harooni et al. | 351/205 |

FOREIGN PATENT DOCUMENTS

| | | |
|---|---|---|
| GB | 2 141 225 | 12/1984 |
| JP | 58-89237 | 5/1983 |
| JP | 58-103433 | 6/1983 |
| JP | 9-28676 | 2/1997 |
| JP | 09122078 A * | 5/1997 |
| JP | 9-131319 | 5/1997 |
| JP | 9-140672 | 6/1997 |
| JP | 10-43139 | 2/1998 |
| JP | 2802356 | 7/1998 |
| JP | 11-197114 | 7/1999 |
| WO | WO 98/46122 | 10/1998 |

OTHER PUBLICATIONS

Delori, F.C., "Spectrophotometer for noninvasive measurement of intrinsic fluorescence and reflectance of the ocular fundus," *App. Optics*, vol. 33, No. 31, Nov. 1, 1994.

* cited by examiner

*Primary Examiner*—David M. Gray
*Assistant Examiner*—Michelle Nguyen
(74) *Attorney, Agent, or Firm*—Finnegan, Henderson, Farabow, Garrett & Dunner, L.L.P.

(57) ABSTRACT

A fundus camera according to the present invention is capable of facilitating observation, color photographing and fluorescent photographing without complicating operations and components of the device. The fundus camera is provided with a first illumination optical system for illuminating a fundus of an eye to be examined with infrared light for observation, a second illumination optical system for illuminating the fundus of the eye with visible light for photographing, a photographing optical system for photographing an image of the fundus with visible reflection light, from the fundus, and an observation optical system for observing the fundus in the infrared reflection light from the fundus. The observation optical system includes an optical path shared with the photographing optical system and an optical path branched from the optical path of the photographing optical system by a first wavelength-selecting mirror. At least the photographing optical system is provided with a barrier filter which cuts off visible illumination light for fluorescence excitation and which transmits fluorescence from the fundus. The first illumination optical system includes the first illumination source. The second illumination optical system includes the second illumination source and an exciter filter for visible fluorescent excitation disposed in an optical path. The photographing optical system includes a photographing element.

8 Claims, 3 Drawing Sheets

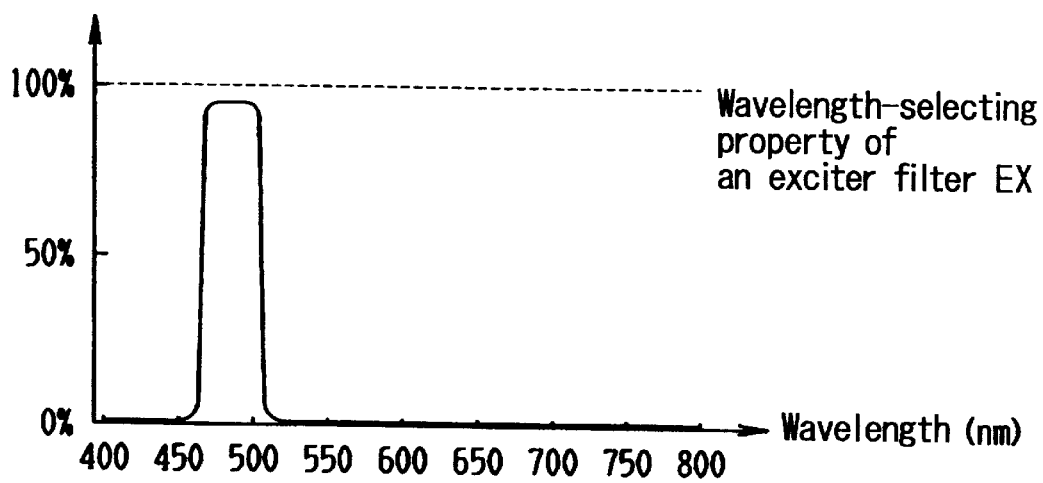
F I G. 3
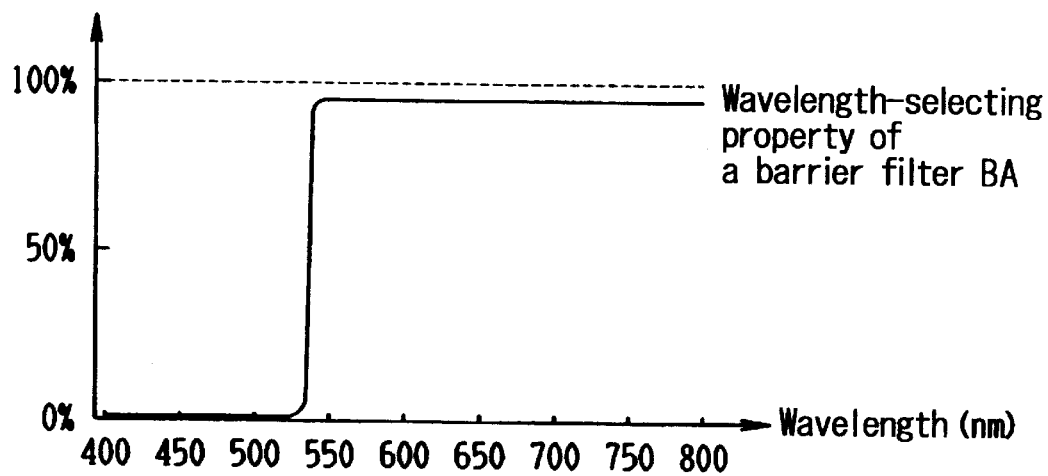
F I G. 4

FUNDUS CAMERA

BACKGROUND OF THE INVENTION

1. Field of the Invention

The present invention relates to a fundus camera for photographing a fundus of an eye to be examined.

2. Description of Related Art

As for fundus cameras, those of non-mydriasis type have been widely used to photograph a fundus with visible light while the fundus is observed in infrared light. Besides, there have also been known those fundus cameras loaded with an additional function of visible fluorescent photographing (fluorescein angiography) (with mydriatics).

Conventionally, this type of fundus camera switches between an optical path of an observation optical system (hereinafter, referred to simply as an observation optical path) and an optical path of a photographing optical system (hereinafter, referred to simply as a photographing optical path) by using a pop-up mirror. In addition, at the time of fluorescent photographing, with such a camera, an infrared transmission filter in an optical path of an illumination optical system (hereinafter, referred to simply as an illumination optical path) is removed from the illumination optical path, and an exciter filter for fluorescence excitation is inserted in the illumination optical path. Then, after an alignment is carried out with a fundus being observed in visible light, a barrier filter for fluorescent photographing is inserted in the photographing optical path.

In this type of fundus camera, however, it is required to execute operations such as driving a pop-up mirror or inserting an exciter filter and a barrier filter synchronously with the firing (lighting) of a flash lamp for photographing. Accordingly, a driving mechanism and a control sequence for those operations should be complicated, which may increase the possibility of causing troubles such as a breakdown due to linkages.

In addition, at the time of fluorescent photographing, it takes much time and trouble to photograph if the exciter filter and the barrier filter are successively inserted manually.

SUMMARY OF THE INVENTION

The present invention has been made in view of the above circumstances and has an object to overcome the above problems and to provide a fundus camera capable of facilitating observation, color photographing, and fluorescent photographing without using any complicated structure.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, a fundus camera for photographing a fundus of an eye to be examined is provided with a first illumination optical system for illuminating the fundus of the eye with infrared illumination light for observation, a second illumination optical system for illuminating the fundus of the eye with visible illumination light for photographing, a photographing optical system for photographing an image of the fundus with the visible reflection light from the fundus, an observation optical system for observing the fundus in the infrared reflection light from the fundus, and a barrier filter for transmitting fluorescence from the fundus as well as for cutting off visible illumination light for fluorescence excitation which has been resulted from or transmitted by an exciter filter.

The first illumination optical system includes a first light source, and the second illumination optical system includes a second light source and the exciter filter for visible fluorescence excitation disposed in an optical path. The photographing optical system includes a photographing element. The observation optical system includes an optical path shared with the photographing optical system and an optical path branched from the optical path of the photographing optical system by a first wavelength-selecting mirror, which has a wavelength-selecting property of transmitting either the infrared wavelength range or the visible wavelength range and reflecting the other. The barrier filter is disposed at least in the optical path of the photographing optical system

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

FIG. 3 is a view illustrating a wavelength-selecting property of an exciter filter EX; and FIG. 4 is a view illustrating a wavelength-selecting property of a barrier filter BA.

DETAILED DESCRIPTION OF THE PREFERRED EMBODIMENTS

Figure 1:
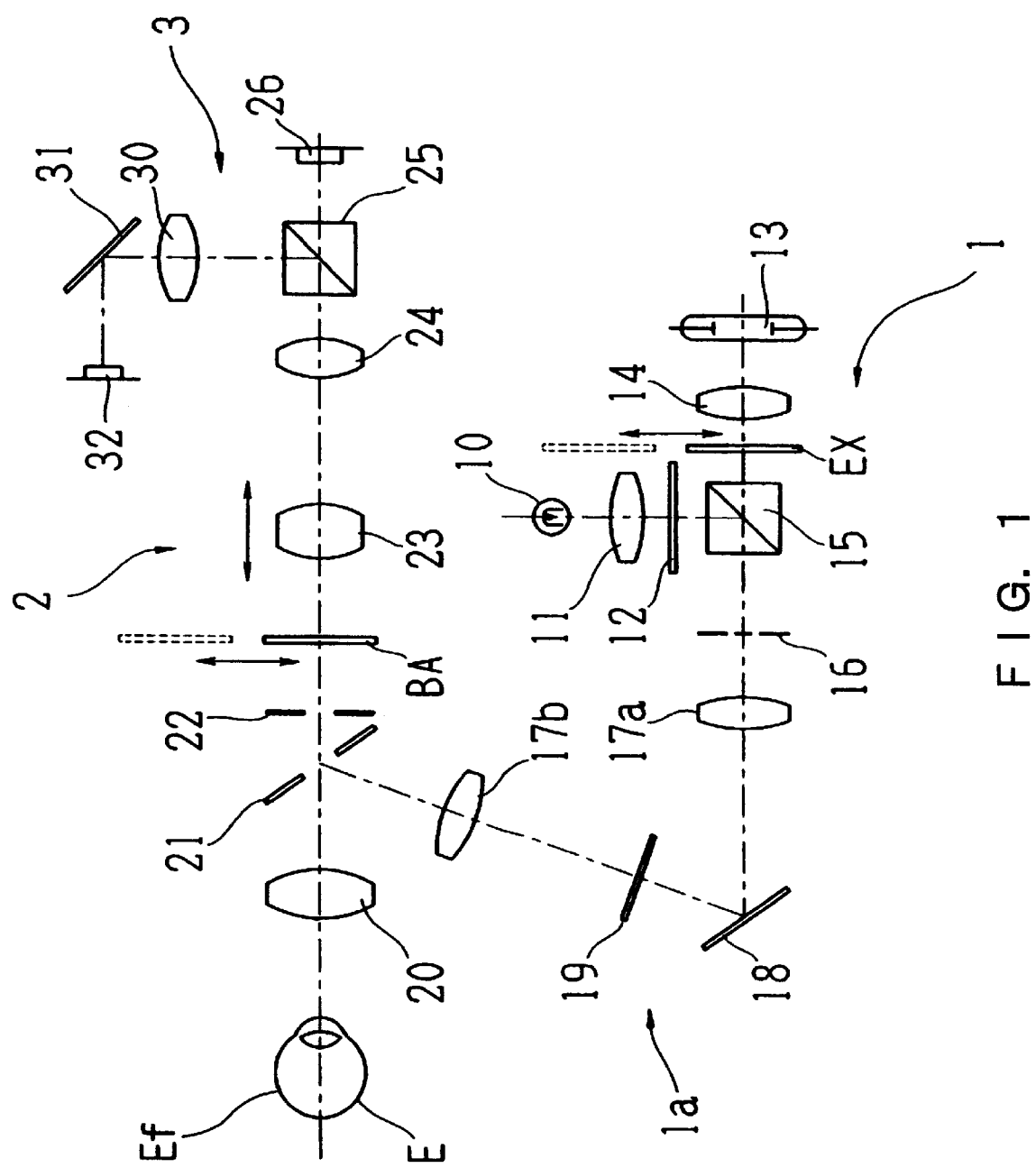
FIG. 1 is a view showing a schematic configuration of an optical system in a fundus camera as one preferred embodiment according to the present invention.

A detailed description of one preferred embodiment of a fundus camera consistent with the present invention will now be given referring to the accompanying drawings. FIG. 1 is a view showing a schematic configuration of an optical system of the fundus camera of the present preferred embodiment, which is provided with an illumination optical system 1, a photographing optical system 2, and an observation optical system 3.

<Illumination Optical System>

Reference numeral 10 is a halogen lamp as a light source for observation. Reference numeral 11 is a condenser lens. Reference numeral 12 is an infrared filter having a wavelength-selecting property of transmitting infrared light. Reference numeral 15 is a dichroic mirror having a wavelength-selecting property of reflecting infrared light and transmitting visible light. Incidentally, instead of the halogen lamp, it is also possible to use an infrared light source such as an infrared LED, which would eliminate the need for the filter 12.

Reference numeral 13 is a flash lamp as a visible light source for photographing. Reference numeral 14 is a condenser lens, and reference letter EX is an exciter filter disposed such that it can be inserted into and removed from the optical path between the dichroic mirror 15 and the flash lamp 13. The exciter filter EX, as shown in FIG. 3, has a wavelength-selecting property of transmitting visible light with wavelengths of approximately 450 nm to 520 nm. Besides, the exciter filter EX is kept out of the optical path at the time of normal color photographing, and in turn, it is kept in the optical path at the time of fluorescent photographing.

An illumination optical system 1a of the illumination optical system 1, which is shared between an infrared illumination optical system and a visible illumination optical system, includes a ring slit 16, a relay lens 17a, a mirror 18, a black dot plate 19 having a small black dot on its center, a relay lens 17b, a mirror 21 with an aperture, and an objective lens 20 shared with the photographing optical system 2.

Infrared illumination light and visible illumination light (when the exciter filter is inserted, the latter becomes excitation light for fluorescence the wavelengths of which have been selected) are made coaxial with each other by the dichroic mirror 15 to illuminate the slit 16. After forming an intermediate image in the vicinity of the aperture of the mirror 21 via the lens 17a, the mirror 18, the black dot plate 19, and the lens 17b, the light passed through the ring slit 16 (ring-slit light) is reflected to be coaxial with the optical axis of the photographing optical system 2. Once converging through the objective lens 20 in the vicinity of the pupil of an eye E to be examined, the light (ring-slit light) which has been reflected by the mirror 21 diffuses and illuminates the fundus Ef of the eye E uniformly. When entering the objective lens 20, the ring-slit light may generate some amount of reflection light which would be detrimental at the time of observing and photographing the image of the fundus Ef. Therefore, the illumination optical system 1 (1a) is designed such that the detrimental light will be absorbed by the small black dot provided on the center of the black dot plate 19.

<Photographing Optical system>

The photographing optical system 2 is provided generally with the objective lens 20, the mirror 21, a photographic diaphragm 22, a barrier filter BA disposed such that it can be inserted into and removed from the optical path, a focusing lens 23 which is movable in the direction of an optical axis, an image forming lens 24, a dichroic mirror (a dichroic prism) 25 having a wavelength-selecting property of reflecting infrared light and transmitting visible light, and a color CCD camera for photographing 26 having a sensitivity to the visible region. As shown in FIG. 4, the barrier filter BA has a wavelength-selecting property of transmitting infrared light and visible light with wavelengths being longer than approximately 520 nm. Besides, the barrier filter BA is kept out of the optical path at the time of normal color photographing, and in turn, it is kept in the optical path at the time of fluorescent photographing.

Incidentally, by using as the camera 26 a non-interlaced progressive scanning camera rather than an interlaced camera for use with an analog TV, a photographed image of the fundus Ef can be used immediately as a digitized electronic image.

<Observation Optical System>

The observation optical system 3 shares optical components from the lens 20 through the dichroic mirror 25 with the photographing optical system 2, and the dichroic mirror 25 bifurcates an optical path. Infrared reflection light from the fundus Ef reflected by the dichroic mirror 25 is relayed by (passed through) a relay lens 30, and it is further reflected by the mirror 31, so that a mirror-inverted image is corrected and that an image of the fundus Ef is formed in a CCD camera for observation 32 which has a sensitivity to the infrared region. The image of the fundus Ef photographed by the camera 32 is displayed in monochrome on a liquid crystal display (LCD) 53.

Figure 2:
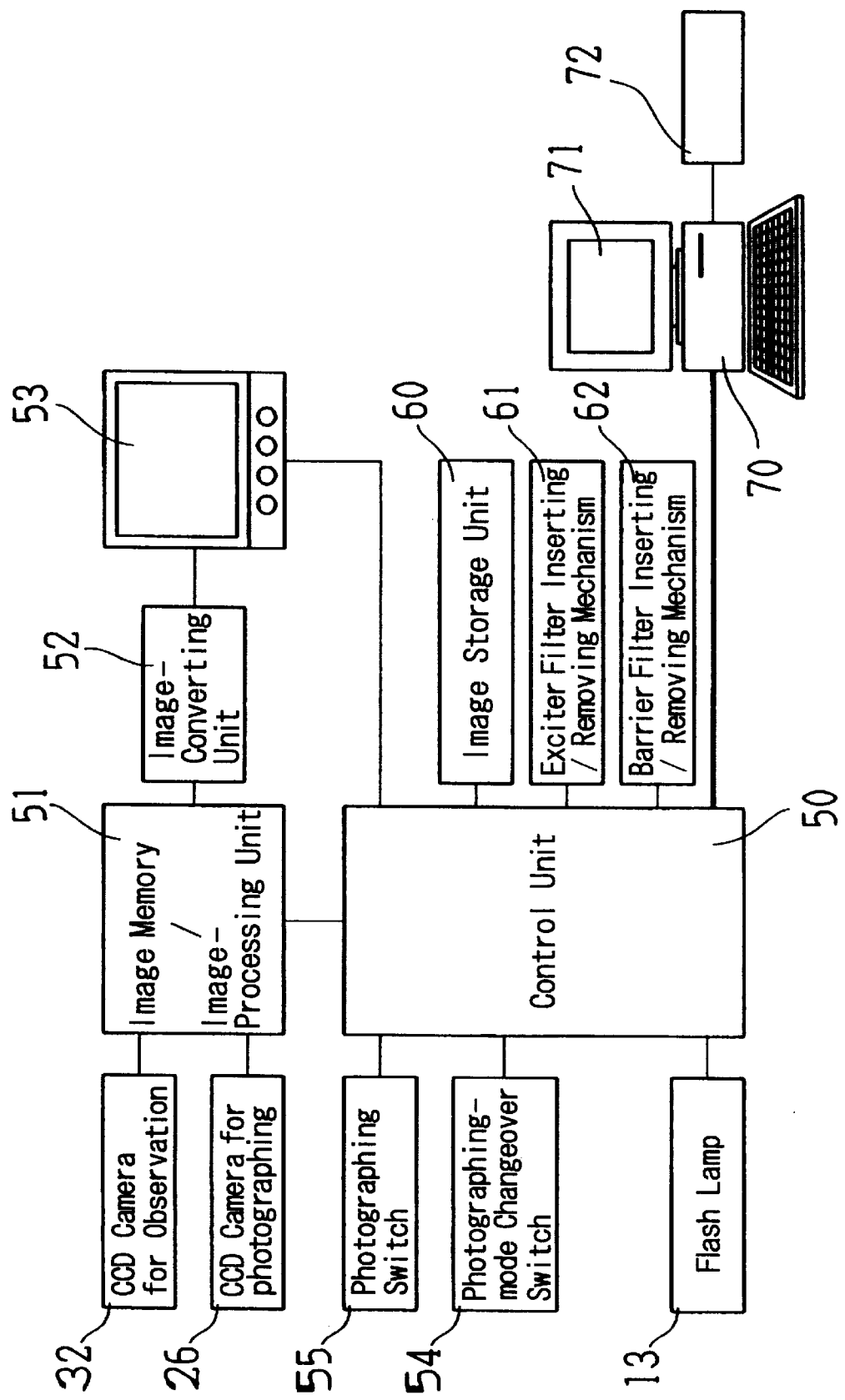
FIG. 2 is a view showing a schematic configuration of primary units of a control system in the fundus camera as the preferred embodiment according to the present invention.

The description will now be given to the operation of the fundus camera having the aforementioned structure with reference to the schematic view of primary units of the control system shown in FIG. 2.

First, reference will now be made to the case of normal color photographing performed without mydriatics. At the time of this type of photographing, the filter EX and the filter BA are removed from their respective optical paths.

The light from the lamp 10 passes the lens 11 and then the filter 12 where its wavelengths in the infrared region are selected, and the resultant infrared light is reflected by the dichroic mirror 15 to illuminate the slit 16. The infrared illumination light, having passed the slit 16, illuminates the fundus Ef uniformly via the lens 17a, the mirror 18, the black dot plate 19, the lens 17b, the mirror 21, and the lens 20.

The infrared reflection light from the fundus Ef passes the lens 20 and the aperture of the mirror 21, and it is then reflected by the dichroic mirror 25 via the diaphragm 22, the lens 23, and the lens 24. After having passed the lens 30, the infrared reflection light is further reflected by the mirror 31 to form an image on the photographing surface of the camera 32. After undergoing A/D conversion, picture signals from the camera 32 are input into the LCD 53 through an image memory/image-processing unit 51 and an image-converting unit 52 for converting picture signals into those for LCD display, so that the image of the fundus Ef (the eye E) is displayed in monochrome.

While observing the image of the fundus Ef (the eye E) on the LCD 53, an examiner performs an alignment. (At this point, the alignment may be carried out utilizing an alignment reflex formed by infrared light which is projected onto a cornea of the eye E by an unillustrated alignment optical system.) If the image of the fundus Ef blurs owing to a refractive error of the eye E during the alignment, the examiner shifts the lens 23 and focuses it on the fundus Ef. (At this time, the lens 23 may be focused on the fundus Ef utilizing a focus index such as a split baseline formed by infrared light which is projected onto the fundus Ef by an unillustrated focusing optical system.)

Once the examiner can observe on the LCD 53 the image of the fundus Ef which he desires to photograph, he inputs a trigger signal by pressing a photographing switch 55. After the trigger signal is input, a control unit 50 fires (lights) the lamp 13. The visible illumination light emitted from the lamp 13 is transmitted by the lens 14 and the dichroic mirror 15, so that it is made coaxial with the optical path of the infrared illumination light. After that, the visible illumination light travels along the same optical path as the infrared illumination light to illuminate the fundus Ef.

The visible reflection light from the fundus Ef is transmitted by the dichroic mirror 25 after passing the lens 20, the aperture of the mirror 21, the diaphragm 22, the lens 23, and the lens 24 in the same manner as the infrared reflection light. Then, the visible reflection light transmitted by the dichroic mirror 25 forms an image of the fundus Ef on the photographing surface of the camera 26. Picture signals from the camera 26 are input and stored as still frames in the image memory/image-processing unit 51 synchronously with the firing (lighting) of the lamp 13. At this point, the control unit 50 switches the picture signals sent from the image memory/image-processing unit 51 to those signals representing the color image photographed by the camera 26. The picture signals of the color image are input through the image-converting unit 52 into the LCD 53 to display in color the image of the fundus Ef.

Next, reference will now be made to the case of fluorescent photographing. At the time of fluorescent photographing, the filter EX and the filter BA are inserted into their respective optical paths. This operation can also be performed manually, but the system may be configured as well such that, in response to signals for selecting a fluorescent-photographing mode via a photographing-mode changeover switch 54, the control unit 50 actuates an exciter-filter inserting/removing mechanism 61 and a barrier-filter inserting/removing mechanism 62 both of which are driven electrically.

Mydriatics are instilled into the eye E to attain enough mydriasis whereafter the lamp 10 is lit, and an alignment is then carried out. The lamp 10 emits infrared illumination light, which passes the filter 12 to illuminate the fundus Ef. The infrared reflection light from the fundus Ef enters the filter BA via the lens 20, the aperture of the mirror 21, and the diaphragm 22. Since the filter BA transmits the light with wavelengths being longer than approximately 520 nm including the infrared region (see FIG. 4), the infrared reflection light is not cut off but transmitted by the filter BA and reflected by the dichroic mirror 25 via the lens 23 and the lens 24. The infrared reflection light reflected by the dichroic mirror 25 forms an image on the photographing surface of the camera 32 via the lens 30 and the mirror 31 to display in monochrome an image of the fundus Ef on the LCD 53.

While observing the image of the fundus Ef on the LCD 53, the examiner shifts the lens 23 and makes an adjustment so as to bring the image of the fundus Ef into focus. Then, he injects fluorescein sodium (a fluorescer) into the veins of the eye E, and when he assumes that a contrast medium (the fluorescer) has reached the veins of the fundus Ef, he operates the switch 55 to input a trigger signal. Receiving the trigger signal, the control unit 50 causes the lamp 13 to emit visible illumination light, which is then limited by the filter EX to blue light being excitation light for fluorescence and which travels along the above-mentioned optical path to illuminate the fundus Ef. The filer BA completely cuts off reflection light which has been resulted from the excitation light and reflected from the fundus Ef, so that the reflection light itself does not enter the respective cameras of 26 and 32.

On the other hand, in the fundus Ef illuminated by the excitation light, which excites the fluorescer circulated to the veins of the fundus Ef, fluorescence of a band beyond 520 nm occurs. This fluorescence enters the filter BA via the lens 20, the mirror 21, and the diaphragm 22 to be transmitted by the filter BA. Thereafter, the fluorescence is transmitted by the dichroic mirror 25 via the lens 23 and the lens 24, so that an image is formed on the photographing surface of the camera 26. At this stage, it is possible to perform fluorescein angiography. The control unit 50 stores a fluorescein angiographic image in the image memory/image-processing unit 51 synchronously with the firing (lighting) of the lamp 13. Then, the control by the control unit 50 switches the picture signals sent from the image memory/image-processing unit 51 to those signals representing the stored image, so that an image of the fundus Ef is displayed in color on the LCD 53 through the image-converting unit 52.

Connected with the control unit 50 is an image storage unit 60 including an MO (magneto-optic disk) and/or a memory card for storing a large amount of image data. The images taken by normal color photographing and fluorescent photographing are captured by the image memory/image-processing unit 51, and then are stored in the image storage unit 60. The stored image data may be sent to and output from an external computer 70 with which the image storage unit 60 is connected. Thus, the examiner can observe the images of the fundus Ef by displaying them as he intends on a display 71 of the computer 70, and he can also print them out through a printer 72. In the case of using a memory card for the image storage unit 60, for example, by having the external computer 70 read and send the data from the memory card, it is made possible to display images of the fundus Ef on the display 71 and to print them out through the printer 72.

As described above, in the fundus camera according to the present preferred embodiment, by using the dichroic mirror to switch between the optical path of the infrared observation optical system and the optical path of the visible photographing optical system, it is made possible to avoid any complicated structure such as a driving mechanism for inverting a mirror or a driving sequence synchronized with the flash lamp. In addition, this type of fundus camera does not need any mechanism for driving the exciter filter and the barrier filter synchronously with the flash lamp at the time of fluorescent photographing. That is, even with the respective filters inserted in their corresponding optical paths in advance, it is possible to carry out observations in infrared light and fluorescent photographing in the same manner as in the case of normal color photographing.

It should be noted that the system can also be constructed such that the filter BA is disposed between the dichroic mirror 25 and the camera 26. In this case, the filter BA should have at least a wavelength-selecting property of cutting off visible light with approximately 450–520 nm wavelengths or transmitting only fluorescence. With the filter BA disposed as such, however, optical errors would be prone to occur at the time of fluorescent photographing. That is, since the filter BA is disposed in the optical path dedicated for photographing, an image photographed with fluorescence may be out of focus as against focusing of an image for observation photographed by the camera 32. To the contrary, by disposing the filter BA in the optical path shared between the observation optical system and the photographing optical system, it is made possible to make the same optical changes in two rays of reflection light from the fundus Ef which enter the respective cameras of 26 and 32, and thereby reducing an optical difference between the image for observation and the image photographed with fluorescence.

Having now fully described the invention, according to the present invention, observation, color photographing and fluorescent photographing can be easily performed without using any complicated structure.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A fundus camera for photographing a fundus of an eye to be examined, the fundus camera comprising:
   a first illumination optical system for illuminating the fundus with infrared illumination light, the first illumination optical system including a first light source;

a second illumination optical system for illuminating the fundus with visible illumination light, the second illumination optical system including a second light source and an exciter filter for visible fluorescence excitation;

a photographing optical system for photographing an image of the fundus with reflection light of the visible illumination light from the fundus, the photographing optical system including a photographing element;

an observation optical system for observing the fundus in reflection light of the infrared illumination light from the fundus, the observation optical system including an optical path shared with the photographing optical system and an optical path branched from an optical path of the photographing optical system by a first wavelength-selecting mirror having a wavelength-selecting property of transmitting either an infrared wavelength range or visible wavelength range and reflecting the other;

a barrier filter for transmitting fluorescence from the fundus as well as for cutting off reflection light of visible illumination light for fluorescence excitation which has resulted from or has been transmitted by the exciter filter, the barrier filter being disposed at least in the optical path of the photographing optical system; and a second wavelength-selecting mirror having a wavelength-selecting property of transmitting either the infrared wavelength range or the visible wavelength range and reflecting the other, the second wavelength-selecting mirror being disposed in an optical path shared between the first illumination optical system and the second illumination optical system so that optical axes of both the optical systems are coaxial with each other, and wherein the exciter filter is disposed in an optical path between the second wavelength-selecting mirror and the second light source.

2. The fundus camera according to claim 1, wherein the barrier filter is disposed in the optical path shared between the photographing optical system and the observation optical system so as to cut off the reflection light of the visible illumination light for fluorescence excitation and so as to transmit the fluorescence and the reflection light of the infrared illumination light from the fundus.

3. The fundus camera according to claim 1, wherein the first light source includes a lamp emitting white illumination light, and the first illumination optical system further includes an infrared transmission filter disposed in an optical path between the second wavelength-selecting mirror and the first light source.

4. The fundus camera according to claim 1, wherein the exciter filter can be inserted into and removed from the optical path of the second illumination optical system; and the barrier filter can be inserted into and removed from at least the optical path of the photographing optical system.

5. The fundus camera according to claim 4, further comprising a changeover unit with which a photographing mode is switched between a color-photographing mode and a fluorescent-photographing mode, and a moving unit which inserts the exciter filter and the barrier filter into the corresponding optical paths at the time of the fluorescent-photographing mode.

6. The fundus camera according to claim 1, wherein the exciter filter has a wavelength-selecting property of transmitting blue wavelength range only, and the barrier filter has a wavelength-selecting property of cutting off at least the blue wavelength range.

7. The fundus camera according to claim 1, wherein the exciter filter has a wavelength-selecting property of transmitting a wavelength range of approximately 450 nm to 520 nm, and the barrier filter has a wavelength-selecting property of transmitting a wavelength range being longer than approximately 520 nm.

8. A fundus camera for photographing a fundus of an eye to be examined, the fundus camera comprising:

a first illumination optical system for illuminating the fundus with infrared illumination light, the first illumination optical system including a first light source;

a second illumination optical system for illuminating the fundus with visible illumination light, the second illumination optical system including a second light source and an exciter filter for visible fluorescence excitation;

a photographing optical system for photographing an image of the fundus with reflection light of the visible illumination light from the fundus, the photographing optical system including a photographing element;

an observation optical system for observing the fundus in reflection light of the infrared illumination light from the fundus, the observation optical system including an optical path shared with the photographing optical system and an optical path branched from the optical path of the photographing optical system by a first wavelength-selecting mirror having a wavelength-selecting property of transmitting either an infrared wavelength range or a visible wavelength range and reflecting the other; and a barrier filter for transmitting fluorescence from the fundus as well as for cutting off visible illumination light for fluorescence excitation which has resulted from or has been transmitted by the exciter filter, the barrier filter being disposed at least in the optical path of the photographing optical system;

wherein the exciter filter has a wavelength-selecting property of transmitting blue wavelength range only, and wherein the barrier has a wavelength-selecting property of cutting off at least the blue wavelength range.

* * * * *

UNITED STATES PATENT AND TRADEMARK OFFICE
CERTIFICATE OF CORRECTION

PATENT NO. : 6,574,432 B2
DATED : June 3, 2003
INVENTOR(S) : Tsuguo Nanjo

It is certified that error appears in the above-identified patent and that said Letters Patent is hereby corrected as shown below:

<u>Title page,</u>
Item [75], Inventors, "Tsuguo Nanjyo,"should read -- Tsuguo Nanjo, --.
Item [57], ABSTRACT,
Line 11, "light,from" should read -- light from --.

<u>Column 7,</u>
Line 17, "or visible" should read -- or a visible --.

<u>Column 8,</u>
Line 48, "off visible" should read -- off reflection light or visible --.
Line 52, "system;" should read -- system, --.
Line 55, "barrier has" should read -- barrier filter has --.

Signed and Sealed this

Twenty-third Day of March, 2004

JON W. DUDAS
*Acting Director of the United States Patent and Trademark Office*